US009810705B2

(12) United States Patent
Meyer et al.

(10) Patent No.: US 9,810,705 B2
(45) Date of Patent: *Nov. 7, 2017

(54) IN-VITRO DIAGNOSTIC ANALYSIS METHOD AND SYSTEM

(71) Applicant: Roche Diagnostics Operations, Inc., Indianapolis, IN (US)

(72) Inventors: Thomas Meyer, Walchwil (CH); Gottlieb Schacher, Kriens (CH); Rolf Sigrist, Vitznau (CH); Christian Guzek, Birmensdorf (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/249,565

(22) Filed: Aug. 29, 2016

(65) Prior Publication Data

US 2016/0370391 A1 Dec. 22, 2016

Related U.S. Application Data

(63) Continuation of application No. 14/732,132, filed on Jun. 5, 2015, now Pat. No. 9,459,270.

(30) Foreign Application Priority Data

Jun. 11, 2014 (EP) .................................... 14171899

(51) Int. Cl.
*G01N 35/02* (2006.01)
*G01N 35/10* (2006.01)
(Continued)

(52) U.S. Cl.
CPC ......... *G01N 35/0092* (2013.01); *G01N 33/86* (2013.01); *G01N 35/026* (2013.01);
(Continued)

(58) Field of Classification Search
CPC ............... G01N 35/0092; G01N 35/26; G01N 35/1011; G01N 35/1072;
(Continued)

(56) References Cited

U.S. PATENT DOCUMENTS 9,459,270 B2 * 10/2016 Meyer ................ G01N 35/0092
2005/0265900 A1 * 12/2005 Gard ..................... B01L 3/0234
422/400

(Continued)

FOREIGN PATENT DOCUMENTS

WO 93/22686 A2 11/1993

*Primary Examiner* — Maureen Wallenhorst
(74) *Attorney, Agent, or Firm* — Roche Diagnostics Operations, Inc.

(57) ABSTRACT

A method and system for automatic in-vitro diagnostic analysis are described. The method includes adding a first reagent type and a second reagent type to a first test liquid during a first and second cycle times respectively. The addition of the first reagent type to the first test liquid includes parallel addition of a second reagent type to a second test liquid during the first cycle time. The addition of the second reagent type to the first test liquid includes parallel addition of a first reagent type to a third test liquid during the second cycle time, respectively.

20 Claims, 5 Drawing Sheets

(51) Int. Cl.
*G01N 35/00* (2006.01)
*G01N 33/86* (2006.01)

(52) U.S. Cl.
CPC ..... *G01N 35/1002* (2013.01); *G01N 35/1065* (2013.01); *G01N 2035/0094* (2013.01); *G01N 2035/00356* (2013.01); *G01N 2035/00524* (2013.01); *Y10T 436/113332* (2015.01); *Y10T 436/114165* (2015.01); *Y10T 436/115831* (2015.01); *Y10T 436/2575* (2015.01)

(58) Field of Classification Search
CPC .......... G01N 2035/00356; G01N 2035/00524; G01N 2035/0094; G01N 33/48; G01N 33/49; G01N 33/86; Y10T 436/113332; Y10T 436/115831; Y10T 436/114165; Y10T 436/2575
USPC ......... 436/43, 47, 48, 50, 69, 164, 174, 180; 422/63, 65, 67, 68.1, 73, 82.09, 501, 509, 422/515; 73/864.21, 864.22, 864.25
See application file for complete search history.

(56) References Cited

U.S. PATENT DOCUMENTS

| | | |
|---|---|---|
| 2012/0237397 A1 | 9/2012 | Schenk |
| 2013/0017535 A1 | 1/2013 | Frey |
| 2014/0073043 A1 | 3/2014 | Holmes |

\* cited by examiner

IN-VITRO DIAGNOSTIC ANALYSIS METHOD AND SYSTEM

CROSS-REFERENCE TO RELATED APPLICATIONS

This application is a continuation of U.S. application Ser. No. 14/732,132, filed Jun. 5, 2015, now U.S. Pat. No. 9,459,270, issued on Oct. 4, 2016, which is a continuation to EP 14171899.9, filed Jun. 11, 2014, which are hereby incorporated by reference.

BACKGROUND

The present disclosure generally relates to a method and to a system for in-vitro diagnostic analysis involving pipetting of reagents.

In analytical laboratories, in particular in-vitro diagnostic laboratories, a multitude of analyses on biological samples are executed in order to determine physiological and biochemical states of patients, which can be indicative of a disease, nutrition habits, drug effectiveness, organ function and the like.

Sample processing throughput, i.e., the number of biological samples analyzed per hour, as well as the number of different tests that can be carried out, are generally important. For laboratories handling thousands of samples each day, a small delay for each individual sample makes a substantial difference in terms of overall laboratory efficiency.

In order to meet this demand, optimal hardware design and efficient workflow planning are required when developing an automated system for in-vitro diagnostics. In particular, an automated system for in-vitro diagnostic analysis may be required to execute a large number of scheduled process operations, which are repeated at intervals called cycle times and it is important that the cycle times at parity of process operations be as short as possible in order to maximize throughput. Also, it is frequent that different tests require different test conditions, for example, different reaction times, different types of reagents, different volumes, different detection times, and the like. Thus, the system should be also able to dynamically adapt the scheduled workflow due to the various test requirements and variable sequence of test orders and be able to respond quickly to anomalies, errors due to unexpected events, and the like.

Therefore, this is a need for an in-vitro diagnostic analysis system and method that achieves higher processing throughput and workflow efficiency by a programmed control of functional units operating synergistically in parallel on different samples across different cycle times while enabling a time-saving anticipation of subsequent workflow operations.

SUMMARY

According to the present disclosure, a system and an automatic in-vitro diagnostic analysis method are presented. The method can comprises adding a first reagent type to a first test liquid during a first cycle time. The addition of the first reagent type to the first test liquid can comprise parallel addition of a second reagent type to a second test liquid during the first cycle time. The method can also comprise adding a second reagent type to the first test liquid during a second cycle time. The addition of the second reagent type to the first test liquid can comprise parallel addition of a first reagent type to a third test liquid during the second cycle time.

Accordingly, it is a feature of the embodiments of the present disclosure to provide for an in-vitro diagnostic analysis system and method that achieves higher processing throughput and workflow efficiency by a programmed control of functional units operating synergistically in parallel on different samples across different cycle times while enabling a time-saving anticipation of subsequent workflow operations. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A "system for in-vitro diagnostics" can be an analytical apparatus, i.e. a laboratory automated instrument dedicated to the analysis of test liquids for in vitro diagnostics. Examples of such analytical apparatuses can be clinical chemistry analyzers, coagulation analyzers, immunochemistry analyzers, hematology analyzers, urine analyzers and nucleic acid analyzers that can be used for the qualitative and/or quantitative detection of analytes present in the test liquids, to detect the result of chemical or biological reactions and/or to monitor the progress of chemical or biological reactions. The analytical apparatus can comprise functional units for pipetting and/or mixing of samples and/or reagents. The analytical apparatus may comprise a reagent holding unit for holding reagents to perform the analysis. Reagents may be arranged, for example, in the form of containers or cassettes containing individual reagents, or group of reagents, and placed in appropriate receptacles or positions within a storage compartment or conveyor. It may comprise a consumable feeding unit, for example, for feeding reaction vessels. The analytical apparatus can further comprise one or more mixing units, comprising, for example, a shaker to shake a vessel containing a test liquid, or a mixing paddle to mix liquids in a vessel or reagent container. The analytical apparatus can further comprise a detection system and can follow a workflow, for example, execute a number of processing steps, which can be optimized for certain types of analysis such as, for example, clinical chemistry, immunochemistry, coagulation, hematology, and the like.

The analytical apparatus may have different configurations according to the need and/or according to the desired laboratory workflow. Additional configurations may be obtained by coupling a plurality of apparatuses together and/or adding modules. A "module" can be a work cell, typically smaller in size and weight than an entire analytical apparatus, which can have an auxiliary function to the analytical function of an analytical apparatus and can work only together with an analytical apparatus. A module can be configured to cooperate with one or more analytical apparatuses for carrying out dedicated tasks of a sample processing workflow, which can occur for example before or after analysis of the sample, e.g. by performing one or more pre-analytical and/or post-analytical steps. Examples of the pre-analytical and/or post-analytical steps can be loading and/or unloading and/or transporting and/or storing sample tubes or racks comprising sample tubes, loading and/or unloading and/or transporting and/or storing reagent containers or cassettes, loading and/or unloading and/or transporting and/or storing and/or washing reaction vessels, e.g. cuvettes, loading and/or unloading and/or transporting and/or storing pipette tips or tip racks, reading and/or writing information bearing labels, e.g. barcodes or RFID tags, washing pipette tips or needles or reaction vessels, e.g. cuvettes, mixing paddles, mixing of samples with other liquid, e.g. reagents, solvents, diluents, buffers, decapping, recapping, pipetting, aliquoting, centrifuging, and so on. An example of such a module can be a sample loading and/or unloading unit for loading/unloading sample tubes.

According to some embodiments, the system can comprise a vessel processing area comprising at least one static vessel holder and at least one movable vessel workstation that can comprise a vessel gripper.

The term "vessel" can be herein used to indicate a container comprising a body and an inner space to receive liquids, e.g. to enable a reaction between one or more samples and one or more reagents and/or to enable analyis of a test liquid contained therein. According to some embodiments, the vessel can be a cuvette, i.e. a container that can, at least, in part, be optically transparent and shaped to allow the photometric measurement, such as, for example, the measurement of changes in optical transmission, such as absorbance and scattering, of a test liquid contained therein. The cuvette may be used in the performance of absorbance or scattering assays to detect the result of a chemical or biological reaction or to monitor the progress of a chemical or biological reaction, e.g. in a coagulation assay, agglutination assay, turbidimetric assay. According to one embodiment, the cuvette body can comprise side walls, a closed bottom and an upper opening for allowing liquids to be introduced in an inner space formed by the side walls and the closed bottom. According to one embodiment, the cuvette can comprise at least one lip projecting outwards of the cuvette body in proximity of the upper opening. This lip may be convenient for gripping the cuvette by the vessel gripper and/or for holding the cuvette in the static cuvette holder. The cuvette may have an inner volume in the milliliter or microliter range.

A "static vessel holder" can be a holding device comprising one or more static vessel holding positions such as, for example, in the form of a recess, cavity, frame, seat or the like. The term "static" can mean immovable with respect to the rest of the system. The static vessel holder may be, for example, embodied as a fixed unit or block in a vessel processing area. The unit or block may have one or more other functions in addition to the holding function. The static vessel holder may, for example, act as an incubation station to hold one or more vessels at a certain temperature for a certain time, sufficiently long, e.g., for a reaction between a test liquid and a reagent to be completed or to reach an acceptable degree of completion under the reaction conditions, and where the time can extend over more than one cycle time. The static vessel holder may also or, in alternative, act as a detection station to allow detection such as, for example, a photometric measurement, of a test liquid in a vessel. According to some embodiments, the static vessel holder can comprise at least one vessel holding position acting as an incubation position and/or at least one vessel holding position acting as a detection position, where the static vessel holder may be divided in functional subunits on the same block or different blocks, e.g., one subunit for incubation and one subunit for detection. According to some embodiments, the at least one static vessel holder can comprise a plurality of linearly arranged vessel holding positions.

A "movable vessel workstation" can be a functional unit operatively coupled to the static vessel holder and that can move with respect to the static vessel holder. According to some embodiments, the at least one vessel workstation can be translatable relative to the at least one static vessel holder to transfer vessels between different vessel holding positions of the at least one static vessel holder. The movable vessel work station can comprise a gripper for gripping vessels, e.g., a vessel at a time, by which it is possible to place vessels into the vessel holding positions, remove vessels from the vessel holding positions and move vessels between vessel holding positions. The gripper can be embodied as a movable element of the movable vessel workstation capable at least to be translatable in the vertical direction and comprising jaws that can be opened and closed to grip or release a vessel.

According to some embodiments, the movable vessel workstation can comprise a shaking mechanism for shaking the vessel held by the gripper at least in part during transfer of the vessel between different vessel holding positions of the static vessel holder. According to an embodiment, the shaking mechanism can be an eccentric rotatable mechanism driven by a motor and coupled to the gripper for eccentrically agitating the gripper and thereby a vessel can be held by the gripper resulting in a mixing of a liquid contained therein.

According to some embodiments, the vessel processing area can further comprise a vessel input station for feeding at least one vessel at a time to the at least one static vessel holder. The "vessel input station" can be a functional unit coupled to the at least one static vessel holder for feeding new vessels to the at least one static vessel holder, e.g., for placing at least one new vessel at a time in at least one vessel holding position of the at least one static vessel holder. According to an embodiment, the vessel input station can be common to at least two static vessel holders. The vessel input station may be coupled to a vessel distribution unit for feeding individual vessels to the vessel input station starting from a bulk supply. The vessel input station may be embodied as a workstation with a translatable and/or rotatable vessel gripper.

The system for in-vitro diagnostics can comprise at least one pipette head comprising at least two pipetting devices movable in a space above the vessel processing area. A "pipetting device" can be a functional unit of the system for pipetting test liquids and/or reagents comprising at least one dispensing nozzle that may function also as an aspiration nozzle. The nozzle may be embodied as a reusable washable needle such as, for example, a steel hollow needle, or as a pipette tip such as, for example, a disposable pipette tip that can be regularly replaced, for example before pipetting a different test liquid or reagent. At least two pipetting devices can be mounted to a pipette head. According to some embodiments, the pipette head can be moved by a head translation mechanism in one or two directions of travel in a plane, such as with guiding rails, and possibly in a third direction of travel orthogonal to the plane, for example with a spindle drive. According to an embodiment, the pipetting head can be moved by a head translation mechanism in one or two directions of travel in a horizontal plane and the pipetting devices can be individually movable in the vertical direction of travel orthogonal to the plane. The term "mounted to" can herein be broadly used to intend attached to, coupled to, or the like without referring to a particular position.

The system for in-vitro diagnostics can further comprise a controller. A "controller" can be a programmable logic controller running a computer-readable program provided with instructions to perform operations in accordance with an operation plan. The controller can be programmed to control the at least one vessel workstation, the at least one pipette head and the at least two pipetting devices for executing a number of scheduled process operations. The scheduled process operations can comprise the addition of a first reagent type and a second reagent type to a first test liquid during a first and second cycle time respectively, the addition of the first reagent type to the first test liquid comprising parallel addition of a second reagent type to a second test liquid during the first cycle time and the addition of the second reagent type to the first test liquid comprising parallel addition of the first reagent type to a third test liquid during a second cycle time, respectively.

The operation plan may however further comprise other operations, such as aspirating a test liquid, dispensing a test liquid, aspirating first and second type reagents, washing aspiration/dispensing nozzles and/or replacing disposable tips, and moving the pipetting head to an aspiration, a dispensing, an end or wash position. The operation plan may further comprise operations other than those associated with pipetting and moving of the pipetting devices. For example, the operation plan may comprise one or more of the following: moving of test liquid containers, opening and/or closing of test liquid containers, piercing caps of test liquid containers, moving of vessels, mixing of test liquids, and detecting the result of reactions. The controller may comprise a scheduler for executing a sequence of steps within a predefined cycle time for a number of cycle times. The controller may further determine the order of in vitro diagnostic tests according to the assay type, urgency, and the like. The controller may further dynamically change the operation plan according to unusual occurring circumstances or newly occurring test orders or events.

The term "test liquid" can herein be used to indicate either a sample or a mixture or solution of one or more samples and one or more reagents, object of a test, i.e. an in-vitro diagnostic analysis. The term "sample", as used herein, can refer to a liquid material suitable for pipetting and being subjected to an in vitro diagnostic analysis, e.g. in order to detect one or more analytes of interest suspected to be present therein or to measure a physical parameter of the sample as such, for example, pH, color, turbidity, viscosity, coagulation time, and the like. Examples of in vitro diagnostic tests can be clinical chemistry assays, immunoassays, coagulation assays, hematology assays, nucleic acid testing, and the like. In some embodiments, the disclosed system can be suitable for coagulation in vitro diagnostic tests.

The sample can be derived from any biological source, such as a physiological fluid, including, blood, saliva, ocular lens fluid, cerebral spinal fluid, sweat, urine, milk, ascites fluid, mucous, synovial fluid, peritoneal fluid, amniotic fluid, tissue, cells or the like. The sample can be pretreated prior to use, such as preparing plasma from blood, diluting viscous fluids, lysis or the like; methods of treatment can involve filtration, centrifugation, distillation, concentration, inactivation of interfering components, and the addition of reagents. A sample may be used directly as obtained from the source or following a pretreatment to modify the character of the sample, e.g. after being diluted with another solution or after having being mixed with reagents e.g. to carry out one or more in vitro diagnostic tests. The term "sample" as used herein is therefore not only used for the original sample but also relates to a sample which has already been processed (pipetted, diluted, and mixed with reagents, enriched, having been purified, having been amplified, and the like). According to an embodiment the sample is a citrate treated blood sample.

The term "reagent" can generally be used to indicate a liquid or substance required for treatment of a sample. Reagents may be any liquid, e.g., a solvent or chemical solution, which can be mixed with a sample and/or other reagent in order e.g., for a reaction to occur, or to enable detection. A reagent may be, for example, a diluting liquid, including water, may comprise an organic solvent or a detergent, or it may be a buffer. A reagent in the more strict sense of the term may be a liquid solution containing a reactant, typically a compound or agent capable e.g., of binding to or chemically transforming one or more analytes present in a sample. Examples of reactants can be enzymes, enzyme substrates, conjugated dyes, protein-binding molecules, nucleic acid binding molecules, antibodies, chelating agents, promoters, inhibitors, epitopes, antigens, and the like.

A "first reagent type" or "reagent of the first type" can be a reagent required at an earlier stage of a sample processing workflow for a first reaction to occur and that can typically require a second reagent type or reagent of the second type for a test to be completed. According to an embodiment, the first reagent type can be an incubation reagent, e.g., a reagent that is supposed to remain in contact with a sample under certain condition, e.g., a certain time and at a certain temperature in order for the reaction to be completed or to reach an acceptable degree of completion. A single test may require one or more reagents of the first type, e.g., added sequentially at different times of the reaction. Examples of reagents of the first type can be reagents for the determination of coagulation factors and other coagulation parameters, for example, activated partial thromboplastin time (APTT).

A "second reagent type" or "reagent of the second type" can be a reagent that can be required at a later stage of a sample processing workflow by a test liquid which has already reacted with one or more reagents of the first type in order for a test to be completed, or can be a reagent that can per se be sufficient for a test to be completed without requiring the addition of a reagent of the first type. A second reagent type can have therefore the function of continuing the reaction of the first reagent type or to stop the reaction of the first reagent type or to enable detection of the reaction of the sample with the first reagent type. A second reagent type can be the only one or the last reagent to be used in a test before or during detection. According to an embodiment, the second reagent type can be a time-trigger reagent, also called a start reagent, i.e., a reagent that triggers a time measurement from the moment the second reagent type has been added to the test liquid. An example of time-trigger reagent can be a coagulation trigger reagent, for example, a salt solution such as a NaCl or CaCl2 solution.

A "cycle time" can be a recurring time window, typically having a fixed length, during which a certain number of process operations, also called "jobs" or "work packages," can be repeatedly carried out in a controlled sequence, called "cycle." This may not necessarily mean however that all process operations which are carried out in a cycle can be repeated in another cycle. Some process operations may repeatedly occur at every cycle, others may occur every two or more cycles. Also new process operations may be introduced in a cycle, depending on newly added test orders and/or newly occurring circumstances, so that a cycle may be dynamically adapted. Also, there may be extraordinary cycles or changes during a cycle in response to extraordinary conditions such as, for example, in case of clogging of a pipetting device, in case of errors detected in pipetting or liquid level, in case of errors in handling vessels, or the like. In general, only some process operations among all process operations occurring in a single cycle time can be dedicated to the performance of one test. This can mean that in a single cycle, typically at least two tests can be carried out simultaneously, although typically at different stages, i.e., different process operations can be dedicated to different tests respectively in a single cycle time. Thus, a test can be typically completed over a plurality, e.g., two or more, cycle times, where different process operations for carrying out the test may occur in different cycle times, and with possible time intervals between cycle times, e.g., the time interval, during which a test liquid can be incubated.

When reference is made to a "first cycle time," it can be intended any cycle time and when reference is made to a "second cycle time," it can be intended any cycle time coming after a first cycle time, where "after" can mean the next cycle time or two or more cycle times after the first cycle time.

The term "adding to a test liquid" or "addition to a test liquid" may not necessarily be limited in time with respect to the presence of a test liquid. The addition of a first reagent type may occur before or after the addition of a test liquid as long as the test liquid and the reagent or reagents come together as a result of the addition.

"Parallel adding" or "parallel addition" can mean that a first reagent type and a second reagent type can be added simultaneously to two respective test liquids. The term "simultaneously" however may not necessarily mean starting and ending at the same time as this may depend on several factors, such as, for example, the volumes being added, which may be different. The term can thus include at least in part overlapping or one comprised in the other.

The term "dispensing" can refer to a pipetting operation, which can typically be preceded by an aspiration operation of the liquid being dispensed. Parallel dispensing may not necessarily imply parallel aspiration.

According to some embodiments, the controller can be programmed to control the at least two pipetting devices and the at least one vessel workstation to add the first reagent type into a vessel held by the static vessel holder and to add the second reagent type into a vessel held by the gripper of the movable vessel workstation.

According to some embodiments, the gripper can be controlled to hold the vessel at a different height than the vessel held by the static vessel holder during the parallel addition of the first reagent type and the second reagent type.

According to some embodiments, the controller can be further programmed to control the vessel workstation to move the gripper to a dispensing position for dispensing the second reagent type into the vessel held by the gripper. The dispensing position can be defined based on the position of the vessel held by the static vessel holder that within the same cycle time can require the first reagent type and based on the distance between respective pipetting devices on the same pipette head.

According to some embodiments, where the at least one static vessel holder can comprise at least one detection position, after addition of the second reagent type, the controller can further be programmed to control the vessel workstation for transferring the vessel held by the gripper to the at least one detection position.

According to some embodiments, where the vessel workstation comprises a shaking mechanism, the controller can further be programmed to control the shaking mechanism for shaking the vessel held by the gripper at least in part during transfer of the vessel between different positions of the static vessel holder.

According to an embodiment, the system can comprise a static vessel holder and a sample/reagent pipette head comprising at least two reagent pipetting devices and at least one sample pipetting device.

According to an embodiment, the system can comprise at least two static vessel holders, a reagent pipette head comprising at least three reagent pipetting devices and a sample pipette head comprising at least two sample pipetting devices.

A further system for in-vitro diagnostic analysis is also disclosed. The controller can be programmed to control the at least one vessel workstation, the at least one pipette head and the at least two pipetting devices for executing a number of scheduled process operations comprising adding in parallel at least two reagents into at least two respective vessels, at least one of the vessels being held by a static vessel holder and at least one of the vessels being held by the gripper of a movable vessel workstation.

According to some embodiments, the controller can be programmed to control the at least two pipetting devices to add an incubation reagent into the vessel held by the static vessel holder and a time-trigger reagent into the vessel held by the gripper of the movable vessel workstation. According to some embodiments, the controller can be further programmed to control the movable vessel workstation for holding the vessel by the gripper at a different height than the vessel held by the static vessel holder. According to some embodiments, the at least two pipetting devices can be mounted to a single pipette head and the controller can be further programmed to control the movable vessel workstation to move the vessel held by the gripper to a dispensing position for dispensing the time-trigger reagent into the vessel. The dispensing position can be defined based on the position of the vessel held by the static vessel holder, which within the same cycle time can require an incubation reagent, and based on the distance between the respective pipetting devices on the single pipette head. According to some embodiments, the method can further comprise shaking the vessel held by the gripper while moving the vessel towards a detection position.

A further system for in-vitro diagnostic analysis is also disclosed. The controller can be programmed to control the at least one vessel workstation, the at least one pipette head and the at least two pipetting devices for executing a number of scheduled process operations, comprising adding in parallel a time-trigger reagent and an incubation reagent to at least two test liquids into at least two respective vessels.

According to some embodiments, the controller can be programmed to control the at least two pipetting devices to add the incubation reagent into a vessel held by a static vessel holder and to add the time-trigger reagent into a vessel held by the gripper of a vessel workstation. According to some embodiments, the controller can be further programmed to control the vessel workstation for holding the vessel by the gripper at a different height than the vessel held by the static vessel holder. According to some embodiments, the at least two pipetting devices can be mounted to a single pipette head and the controller can be further programmed to control the vessel workstation to move the vessel held by the gripper to a dispensing position for dispensing the reaction-trigger reagent into the vessel. The dispensing position can be defined based on the position of the vessel held by the static vessel holder, which within the same cycle time can require an incubation reagent and based on the distance between the respective pipetting devices on the single pipette head. According to some embodiments, the method can further comprise shaking the vessel held by the gripper while moving the vessel towards a detection position.

A further system for in-vitro diagnostic analysis is also disclosed. The system can comprise a vessel processing area comprising two static vessel holders and a common vessel input station for feeding vessels to the static vessel holders. The vessel processing area can further comprise two movable vessel workstations, each comprising a vessel gripper and translatable relative to a respective static vessel holder to transfer vessels between different vessel holding positions of the respective static vessel holder. The system can further comprise a reagent pipette head comprising at least three reagent pipetting devices and a sample pipette head comprising at least two sample pipetting devices. With this system, it can be possible to nearly double the overall sample processing throughput (number of tests per hour) compared to a system with one single static vessel holder and one sample/reagent pipette head without doubling the number of functional units. This configuration can be mostly optimized for high-throughput testing of two of the most frequently ordered coagulation tests, like the Prothrombin time (PT) test and the activated partial thromboplastin time (APTT) test, where the PT test can require only a time-trigger reagent and the APTT test can require an incubation reagent in a first stage and a time-trigger reagent in a second stage. An even higher throughput can be achieved if the tests are alternated in a test order sequence. The two static vessel holders may be advantageously dedicated to different tests respectively.

An automatic in-vitro diagnostic analysis method is also disclosed. The method can comprise adding a first reagent type and a second reagent type to a first test liquid during first and second cycle times, respectively. The addition of the first reagent type to the first test liquid can comprise parallel addition of a second reagent type to a second test liquid during the first cycle time and the addition of the second reagent type to the first test liquid can comprise parallel addition of a first reagent type to a third test liquid during the second cycle time, respectively.

According to some embodiments, the parallel addition of the first reagent type and the second reagent type can be carried out with a single pipette head. The single pipette head can comprise at least two pipetting devices. According to an embodiment, the at least two pipetting devices can be independently drivable in the vertical direction.

According to some embodiments, the addition of the first reagent type can comprise dispensing the first reagent type into a vessel held by a static vessel holder and the addition of the second reagent type can comprise dispensing the second reagent type into a vessel held by a gripper of a movable vessel workstation.

According to an embodiment, the first reagent type can be an incubation reagent and the second reagent type can be a time-trigger reagent.

According to some embodiments, the method can comprise holding the vessel by the gripper and the vessel by the static vessel holder at different heights respectively during parallel addition of the second reagent type and the first reagent type respectively.

According to some embodiments, the method can comprise moving the gripper to a dispensing position for dispensing the second reagent type into the vessel held by the gripper. The dispensing position can be defined based on the position of the vessel held by the static vessel holder that within the same cycle time requires the first reagent type and based on the distance between respective pipetting devices on a single pipette head.

According to some embodiments, the method can comprise shaking the vessel held by the gripper while moving the vessel towards a detection position.

A further automatic in-vitro diagnostic analysis method is described. The method can comprise dispensing in parallel with at least two pipetting devices at least two reagents into at least two respective vessels, at least one of the vessels being held by a static vessel holder and at least one of the vessels being held by the gripper of a vessel workstation.

According to some embodiments, the reagent dispensed into the vessel held by the static vessel holder can be an incubation reagent and the reagent dispensed into the vessel held by the gripper of the vessel workstation can be a time-trigger reagent. According to some embodiments, the method can further comprise holding the vessel by the gripper and the vessel by the static vessel holder at different heights respectively during parallel dispensing. According to some embodiments, the at least two pipetting devices can be mounted to a single pipette head and the method can comprise moving the gripper to a dispensing position for dispensing a reagent into the vessel held by the gripper. The dispensing position can be defined based on the position of the vessel held by the static vessel holder that within the same cycle time requires a reagent and based on the distance between respective pipetting devices on the single pipette head. According to some embodiments, the method can further comprise shaking the vessel held by the gripper while moving the vessel towards a detection position.

A further automatic in-vitro diagnostic analysis method is described. The method can comprise adding in parallel with a single pipette head comprising at least two pipetting devices a time-trigger reagent and an incubation reagent to at least two test liquids respectively. According to some embodiments, the method can comprise adding the incubation reagent into a vessel held by a static vessel holder and adding the time-trigger reagent into a vessel held by the gripper of a vessel workstation. According to some embodiments, the method can further comprise holding the vessel by the gripper and the vessel by the static vessel holder at different heights respectively during parallel dispensing. According to some embodiments, the method can comprise moving the gripper to a dispensing position for dispensing the time-trigger reagent into the vessel held by the gripper. The dispensing position can be defined based on the position of the vessel held by the static vessel holder that within the same cycle time requires an incubation reagent, and based on the distance between respective pipetting devices on the single pipette head. According to some embodiments, the method can further comprise shaking the vessel held by the gripper while moving the vessel towards a detection position.

Figure 1:
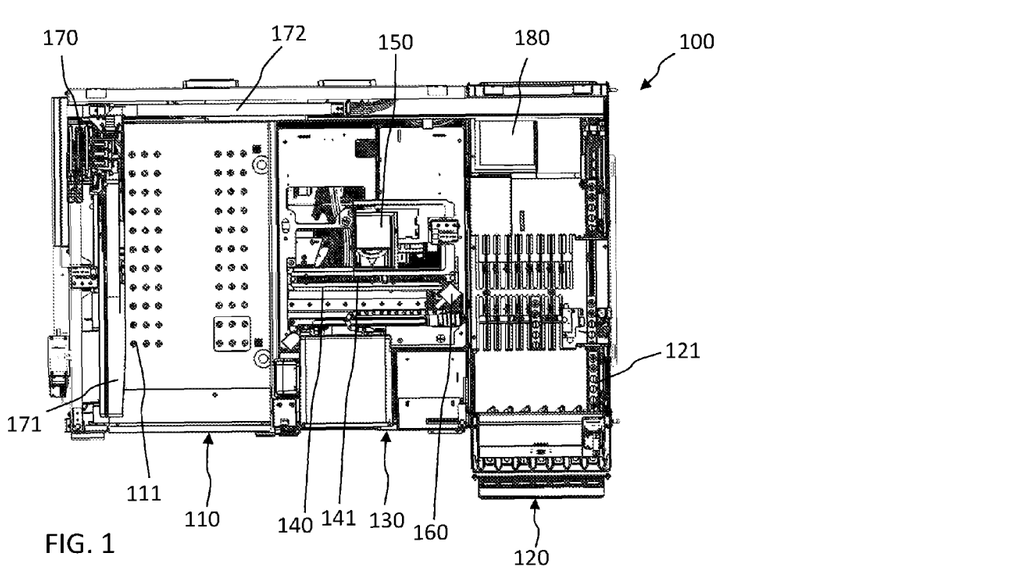
FIG. 1 illustrates a partial top view of a system for in vitro diagnostics according to an embodiment of the present disclosure.

Referring initially to FIG. 1, FIG. 1 shows an example of system 100 for in-vitro diagnostic analysis such as, for example, a coagulation analyzer. The system 100 can comprise a reagent holding unit 110 for holding reagents of the first type and of the second type to perform different coagulation tests. The reagent unit 110 can be embodied as a closed and tempered storage compartment comprising access holes 111 for a pipetting nozzle to enter the compartment and withdraw an aliquot of reagent. The system 100 can further comprise a sample loading/unloading unit 120 for loading/unloading sample tube racks 121 comprising sample tubes. The system can further comprise a central vessel processing area 130 (shown and explained in greater detail in relation to FIG. 5). The vessel processing area 130 can comprise a linear static vessel holder 140. The static vessel holder 140 can comprise a plurality of vessel holding positions 141. The vessel processing area 130 can further comprise a vessel input station 150 for feeding one vessel at a time into the static vessel holder 140. The vessel processing area 130 can further comprise a movable vessel workstation 160 linearly translatable with respect to the static vessel holder 140 and coupled to the static vessel holder 140 to transfer vessels between vessel holding positions 141 of the static vessel holder 140.

Figure 5:
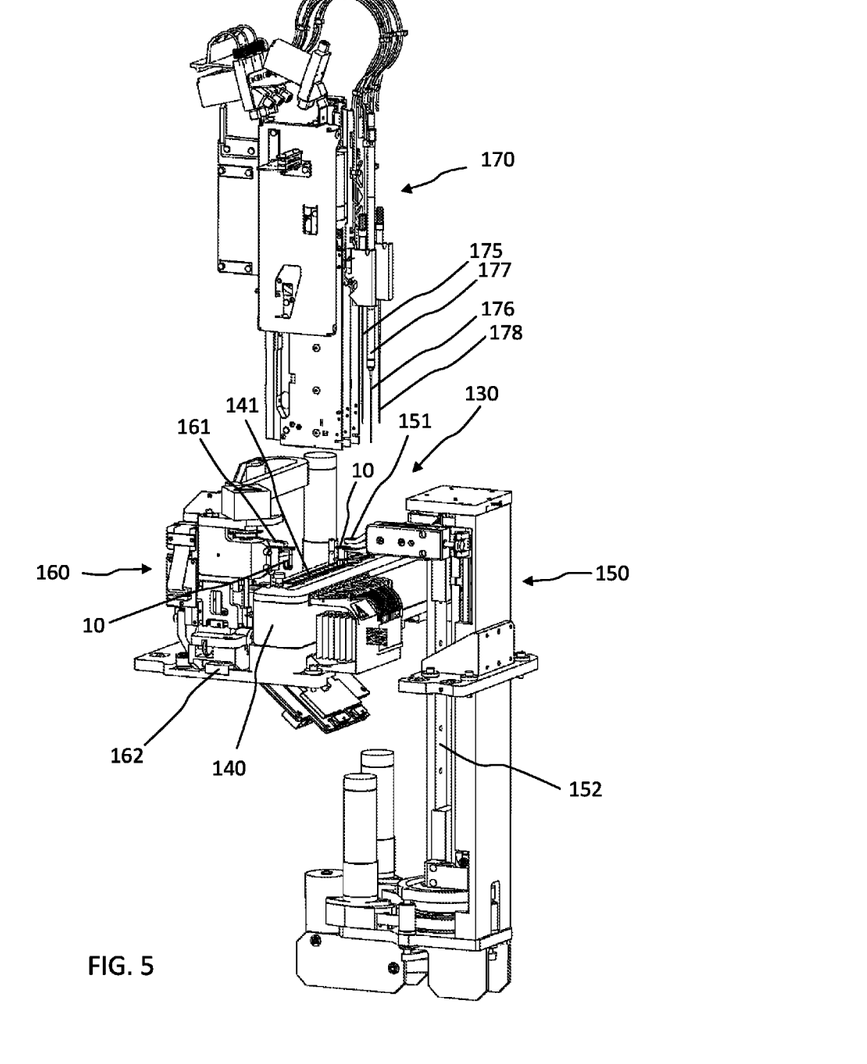
FIG. 5 illustrates some units of the system of FIG. 1 in greater detail according to an embodiment of the present disclosure.

The system 100 can further comprise a pipette head 170 comprising three pipetting devices (shown in FIG. 5). The pipette head 170 can be translatably mounted on a horizontal arm 171 and the arm 171 can be translatably coupled to an orthogonal guide rail 172. The pipette head 170 can thus be movable in a space above the reagent unit 110, above the vessel processing area 130, and above the sample loading/unloading unit 120. In addition, the pipetting devices can each be individually translatable in a vertical direction such as to be able to access a reagent container in the reagent unit 110 via holes 111, a sample tube in the sample loading/unloading unit 120, and a vessel in the vessel processing area 130. Using the same pipette head 170, test liquids can be aspirated from sample tubes in the sample loading/unloading unit 120, reagents can be aspirated from reagent containers in the reagent unit 110 and both test liquids and reagents can be dispensed into vessels in the vessel processing area 130.

Figures 6A, 6B:
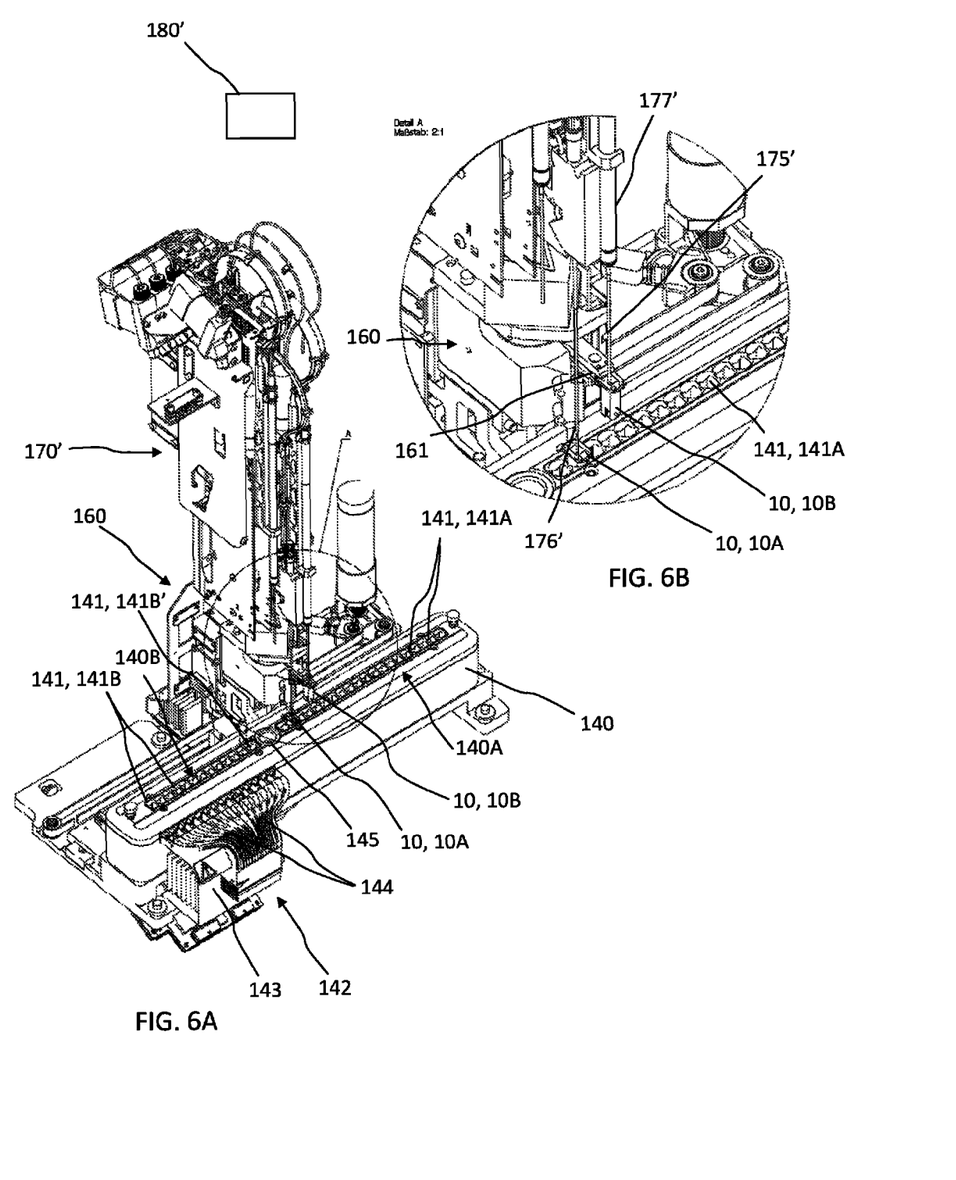
FIG. 6A illustrates shows a method of operation of the system of FIG. 2, which also applies to the system of FIG. 1 according to an embodiment of the present disclosure.
FIG. 6B illustrates a magnification of a detail of FIG. 6A according to an embodiment of the present disclosure.

The system 100 can further comprise a controller 180 programmed to control the execution of a number of scheduled process operations including operation of the movable vessel workstation 160, of the pipette head 170 and of the pipetting devices (described more in detail in relation to FIGS. 5 and 6A).

Figure 2:
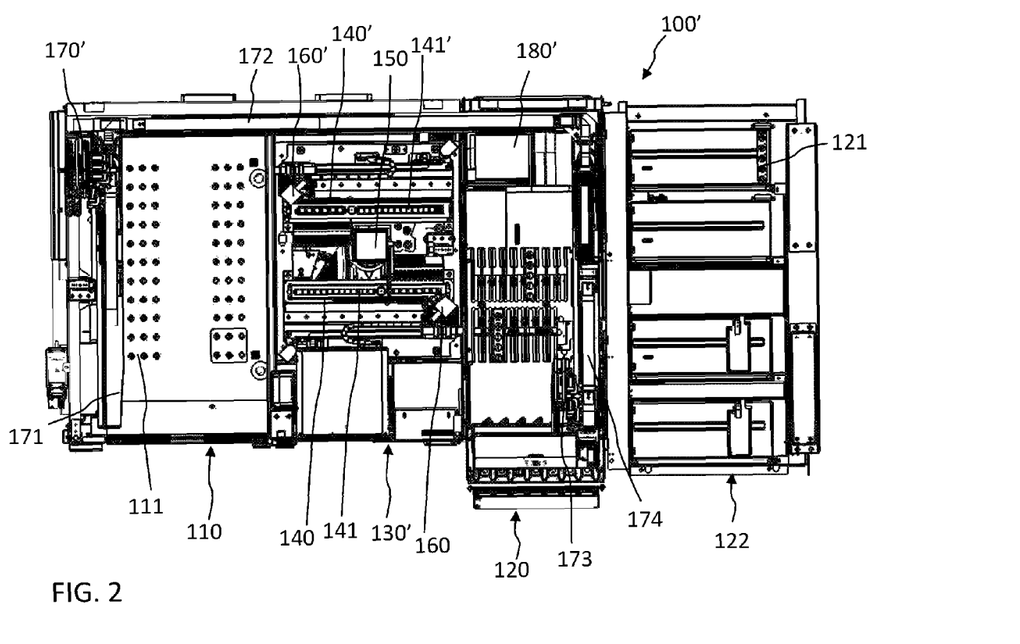
FIG. 2 illustrates a variant of the system of FIG. 1 according to an embodiment of the present disclosure.

FIG. 2 shows another system 100', which is a variant of the system 100 of FIG. 1. One difference between the system 100' and the system 100 is that the system 100' can comprise a vessel processing area 130', which compared to the vessel processing area 130 of the system 100 can further comprise a second linear static vessel holder 140' and a second movable vessel workstation 160' linearly translatable with respect to the second static vessel holder 140' and coupled to the static vessel holder 140' to transfer vessels between vessel holding positions 141' of the second static vessel holder 140'. Another difference between system 100' and system 100 is that the system 100' can comprise two pipette heads 170', 173 translatably mounted on two respective horizontal arms 171, 174. As shown in FIG. 5, the first pipette head 170' can comprise three reagent pipetting devices to aspirate reagents from the reagent unit 110 and to dispense the reagents into vessels in the vessel processing area 130'. The second pipette head 173 can comprise two sample pipetting devices to aspirate test liquids from sample tubes in the sample loading/unloading unit 120 and to dispense the test liquids into vessels in the vessel processing area 130'. The arms 171, 174 can be translatably coupled to the same orthogonal guide rail 172. The two static vessel holders 140, 140' can be arranged parallel to each other and the vessel input station 150, which can be identical to that of FIG. 1, can be symmetrically arranged between the two static vessel holders to feed vessels to both static vessel holders 140, 140'. Another difference between system 100' and system 100 is that the system 100' can further comprise a sample rack tray unit 122, which can be coupled as a module to the sample loading/unloading unit 120 for loading/unloading sample racks 121 into/from the sample loading/unloading unit 120.

Figure 4:
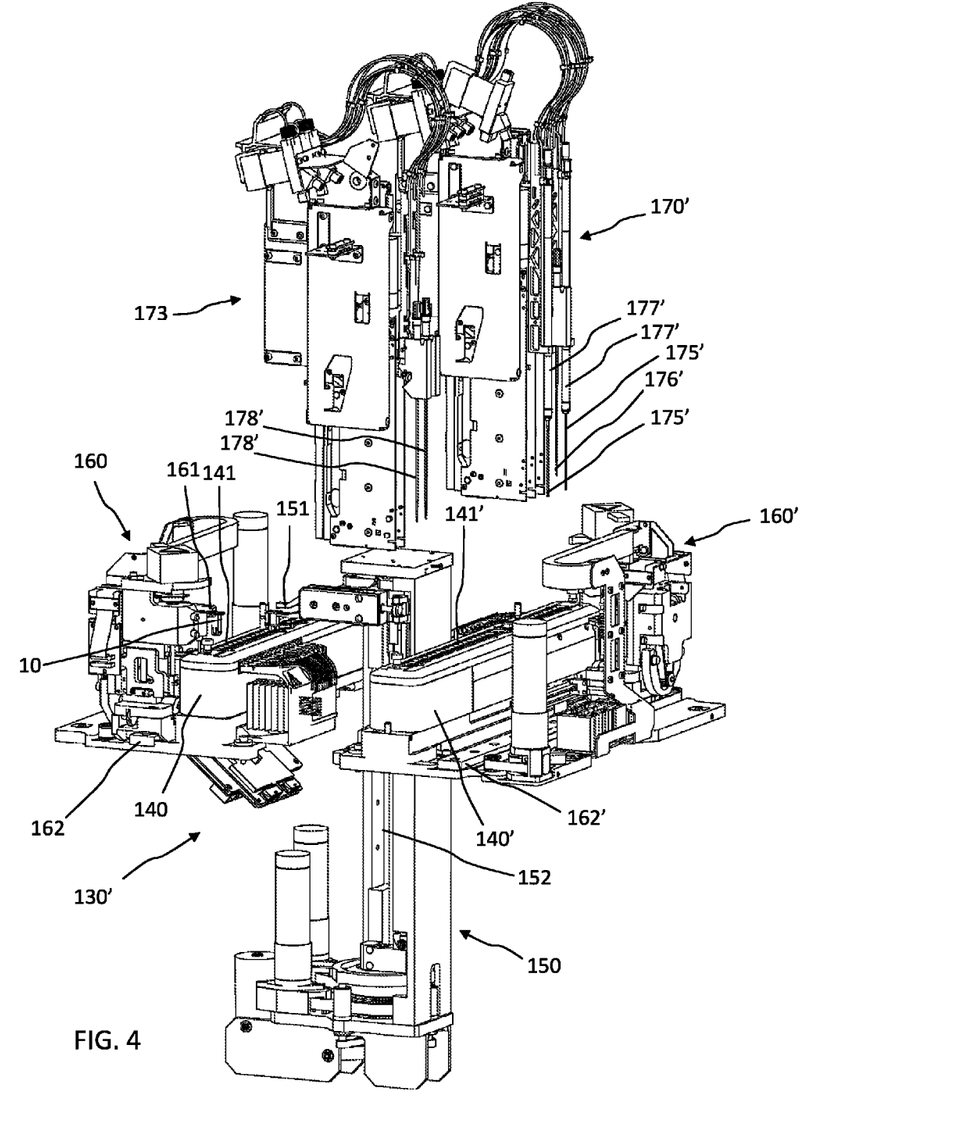
FIG. 4 illustrates some units of the system of FIG. 2 in greater detail according to an embodiment of the present disclosure.

The system 100' can further comprise a controller 180' programmed to control the execution of a number of scheduled process operations including operation of the movable vessel workstations 160, 160', of the pipette heads 170', 173 and of the pipetting devices (described more in detail in relation to FIGS. 4 and 6A-6B).

Figure 3A:
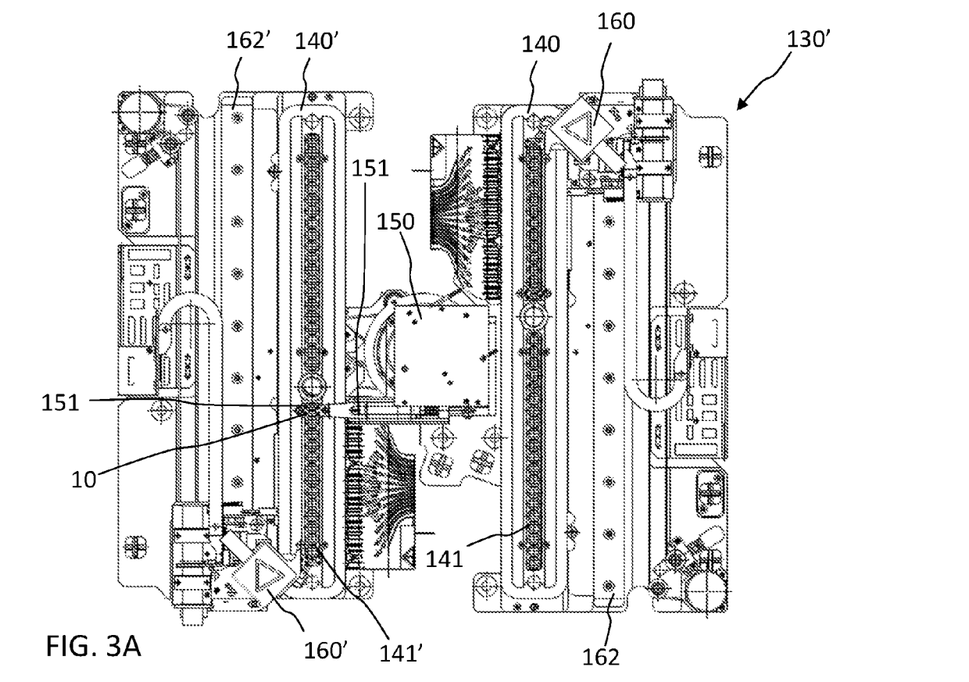
FIG. 3A illustrates a partial top view of a vessel processing area according to the embodiment of FIG. 2 according to an embodiment of the present disclosure.
Figure 3B:
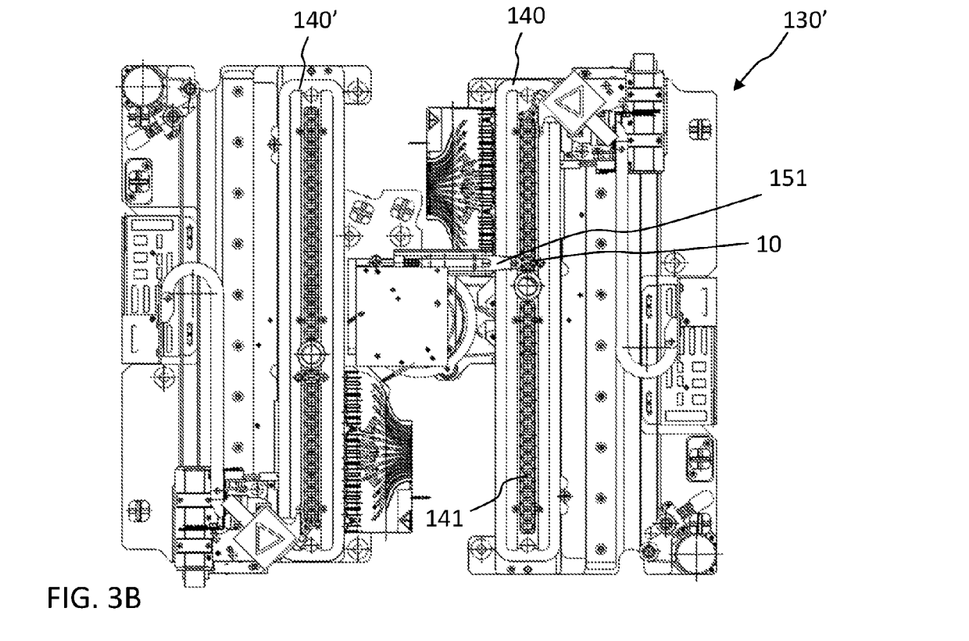
FIG. 3B illustrates the same partial top of view of FIG. 3A except for the position of a vessel gripper according to an embodiment of the present disclosure.

FIGS. 3A-B are partial top views of the vessel processing area 130' (without pipetting devices) according to the embodiment of FIG. 2. FIGS. 3A-B show from top, the arrangement of the two static vessel holders 140, 140' and the two respective movable vessel workstations 160, 160' with respect to each other and with respect to the vessel input station 150. The first static vessel holder 140 and the second static vessel holder 140' can be identical and arranged longitudinally parallel in front of each other. Their orientation can however be inverted, with the second static vessel holder 140' rotated 180 degrees with respect to the first static vessel holder 140. The first and second static vessel holders 140, 140' can be embodied as linear blocks, each comprising an array of linearly arranged vessel holding positions 141, 141' respectively, part of which acting as incubation positions and part of which acting as detection positions (as more in detail described with reference to FIG. 6A).

The vessel input station 150 can comprise a vessel gripper 151 and can be arranged between the first static vessel holder 140 and the second static vessel holder 140' in a symmetrical manner so that upon rotation of the vessel gripper 151 180 degrees, a vessel 10 can be placed by the same vessel gripper 151 either in a vessel holding position 141 of the first static vessel holder 140 or in a vessel holding position 141' of the second static vessel holder 140'. The first movable vessel workstation 160 and the second movable vessel workstation 160' can be identical to each other and arranged parallel to the respective static vessel holders 140, 140' on the outer sides of the respective static vessel holders 140, 140' and opposite to the central vessel input station 150. The first movable vessel workstation 160 can be translatable with respect to the first static vessel holder 140 along guide rail 162 and the second movable vessel workstation 160' can be translatable with respect to the second static vessel holder 140' along guide rail 162' independently from the first movable work station 160. Thus, the first movable workstation 160 can be coupled to the first static vessel holder 140 to transfer vessels between vessel holding positions 141 of the first static vessel holder 140 and the second movable vessel workstation can be coupled to the second static vessel holder 140' to transfer vessels between vessel holding positions 141' of the second static vessel holder 140'.

The vessel input station 150 can be fixed in space with respect to the static vessel holders 140, 140' so that only the vessel gripper 151 can be translated vertically and can be rotated towards either of the static vessel holders 140, 140'. Thus, the vessel input station 150 can place a new vessel 10 one at a time into only one input vessel holding position 141 of the first static vessel holder 140 (FIG. 3B) and into only one input vessel holding position 141' of the second static vessel holder 140' (FIG. 3A). These two input vessel holding positions 141, 141' can be detection positions dedicated to carry out a photometric blank measurement of each new vessel 10 placed in each static vessel holder 140, 140'. The two respective movable vessel workstations 160, 160' can then transfer the vessels 10 from the two input vessel holding positions 141, 141' to any other vessel holding positions 141, 141' according to the scheduled process.

FIG. 4 shows in perspective the vessel processing area 130' of FIG. 3B, with the addition of the two pipette heads 170', 173 above the vessel processing area 130'. The vessel input station 150 can be embodied as a vessel lift comprising a vessel gripper 151 that can be vertically translatable along a guide rail 152 and rotatable in a horizontal plane. The vessel gripper 151 can be coupled to a vessel distribution unit for feeding individual vessels 10 to the gripper 151 at a lower position with respect to the guide rail 152. The vessel gripper 151 can thus transport one vessel 10 at a time from a vessel distribution unit at a lower position to one of the vessel holding positions 141, 141' of the static vessel holders 140, 140' at an upper position.

The movable vessel workstations 160, 160' can be linearly translatable parallel to the static vessel holder 140, 140' respectively along guide rail 162, 162' respectively. Also, the movable vessel workstation 160, 160' can each comprise a vessel gripper 161, 161' respectively that can be translatable in the vertical direction. Thus, the movable vessel workstations 160, 160' can independently move along the respective static vessel holders 140, 140' to bring the vessel grippers 161, 161' in correspondence to any of the vessel holding positions 141, 141' and by vertically translating the vessel grippers 161, 161', they can grip and pull a vessel 10 out of any vessel holding position 141, 141' or place a vessel 10 into any free vessel holding position 141, 141' of the respective static vessel holder 140, 140'. Vessels 10 can thus readily be transferred between different vessel holding positions 141, 141' of the same static vessel holder 140, 140' respectively, e.g., between an incubation position and a detection position, by the movable vessel workstations 160, 160'.

The first pipette head 170' can be a reagent pipette head comprising three reagent pipetting devices and, in particular, two reagent pipetting devices 175' to pipette reagents of the second type and one reagent pipetting device 176' to pipette reagents of the first type. The reagent pipetting devices 175' can each comprise a heating element 177' for heating a reagent of the second type to an optimal temperature between reagent aspiration and reagent dispensing. The second pipette head 173 can be a sample pipette head comprising two sample pipetting devices 178' to pipette samples from sample tubes, e.g., including aspiration through a closure of a sample tube by piercing the closure.

The embodiment of FIG. 4 can achieve double sample processing throughput for at least some tests compared to the embodiment of FIG. 5 without duplicating the number of functional units. At least one reagent needle can be spared and one common vessel input station 150 can be used.

FIG. 5 shows in perspective the vessel processing area of the system 100 of FIG. 1, comprising only one static vessel holder 140, only one movable vessel workstation 160 and only one pipette head 170. The static vessel holder 140, the movable vessel workstation 160 and the vessel input station 150 as well as their functional relationship are the same as in FIG. 4. The pipette head 170 can be a sample/reagent pipette head comprising a first reagent pipetting device 175, a second reagent pipetting device 176 and a sample pipetting device 178. The first reagent pipetting device 175 can pipette reagents of the first type whereas the second reagent pipetting device 176 can pipette reagents of the second type. The second reagent pipetting device 176 can comprise a heating element 177 for heating a reagent of the second type to an optimal temperature between reagent aspiration and reagent dispensing. The sample pipetting device 178 can pipette test liquids from sample tubes, e.g., including aspiration through a closure of a sample tube by piercing the closure.

FIG. 6A and FIG. 6B (a magnification of a detail of FIG. 6A) show further details of part of the embodiment of FIG. 4 during operation, controlled by the controller 180'. Only one static vessel holder 140 with the respective movable vessel workstation 160 and only one pipette head 170' are shown for clarity. The process of parallel addition of a first reagent type and a second reagent type is shown. The same applies also to the embodiment of FIG. 5, except that a different pipette head can be used.

The static vessel holder 140 can comprise a plurality of vessel holding positions 141 for holding a plurality of vessels 10. The static vessel holder 140 can comprise an incubation subunit 140A comprising a plurality of incubation positions 141A (in this example, twenty) embodied as cavities in an aluminum block complementary in shape to the shape of a vessel 10. The incubation subunit 140A can comprise a temperature regulating unit for regulating the temperature of vessels 10 contained in the incubation positions 141A, e.g., for maintaining the vessels 10 at an optimal reaction temperature.

The static vessel holder 140 can further comprise a detection subunit 140B comprising a plurality of detection positions 141B (in this example, thirteen). The detection subunit 140B can comprise a photometric unit 142. The photometric unit 142 can comprise a light source 143 on one side of the detection positions 141B and an optical detector arranged inside the detection subunit 140B on the other side of the detection positions 141B. For each detection position 141B, there can be an optical fiber 144 for guiding light from the light source 143 through a vessel 10 placed in the detection position 141B and an optical detector placed on the opposite side of the detection position to detect light passing through the vessel 10 in the detection position 141B. Thus, each detection position 141B can be arranged in an optical path between an optical fiber 144 and an optical detector. The vessels 10 can therefore conveniently be embodied as cuvettes comprising two parallel and transparent walls, which can be placed in the optical path. Light of different wavelengths may be guided through different optical fibers 144 and/or light of different wavelengths may alternately be guided in the same optical fibers 144. The light source 143 may be common to all optical fibers 144 and can comprise a multi-wavelength light source, e.g., a broad spectrum light source or a plurality of light emitting elements with individual wavelengths or wavelength ranges.

One of the detection positions 141B' can be a blank measurement position for taking a blank measurement of each new vessel 10. In addition, the blank measurement position 141B' can be the input vessel holding position where one new vessel 10 at a time can be placed by the vessel gripper 151 of the vessel input station 150.

The static vessel holder 140 can further comprise a waste port 145 embodied as a hole though the static vessel holder 140 located between the incubation subunit 140A and the detection subunit 140B. The hole 145 can lead to a vessel waste bin located underneath the static vessel holder 140 for disposing used vessels 10 by the vessel gripper 161.

With reference to all embodiments, part of an exemplary process is now described. The following process describes some of the process operations that can occur in a cycle time. The vessel input station 150 can place one new vessel 10 at a time into the input vessel holding position 141B' of the static vessel holder 140 and/or into a corresponding input vessel holding position 141' of the second static vessel holder 140', depending on whether an embodiment with one or two static vessel holders 140, 140' is used. A photometric blank measurement of each new vessel 10 in each static vessel holder 140, 140' can then be first carried out. After taking a photometric blank measurement of the vessel 10, the respective movable vessel workstations 160, 160' can transfer the vessels 10 to a free incubation position 141A, 141' of the respective static vessel holder 140, 140'.

With reference to FIG. 2, FIG. 4, FIGS. 6A-B, the sample pipette head 173 can move to the sample loading/unloading unit 120 and aspirate two test liquids from two sample tubes or two aliquots from the same sample tube with the two respective pipetting devices 178'. The sample pipette head 173 can then move to the first static vessel holder 140 to dispense a test liquid into a vessel 10 in an incubation position 141A and to the second static vessel holder 140' to dispense the other test liquid into another vessel 10 into an incubation position 141' of the second static vessel holder 140' or into another vessel 10 into an another incubation position 141A of the first static vessel holder 140. The reagent pipette head 170' can move to the reagent unit 110 and aspirate one reagent of the first type and two reagents of the second type with reagent pipetting devices 176' and 175' respectively.

The gripper 161 of the first movable vessel workstation 160 can grip a vessel 10B from an incubation position 141A. The first movable vessel workstation 160 can then move to a dispensing position for dispensing the second reagent type into the vessel 10B held by the gripper 161. The dispensing position as shown in FIGS. 6A-B can be defined based on the position of a vessel 10A held in an incubation position 141A of the static vessel holder 140 that within the same cycle time requires the first reagent type, and based on the distance between respective reagents pipetting devices 175', 176' on the reagent pipette head 170'.

The reagent pipette head 170' can move with respect to the first static vessel holder 140 such that a reagent pipetting device 176' containing a reagent of the first type is positioned above the vessel 10A requiring the reagent of the first type and the reagent pipetting device 175' containing the reagent of the second type is placed above the vessel 10B held by the vessel gripper 161 and requiring a reagent of the second type. The reagent pipetting devices 176', 175' can be then lowered at different heights into respective vessels 10A, 10B for the parallel addition of the first reagent type and the second reagent type respectively. The reagent pipetting devices 175', 176' can then be raised and the vessel 10B held by the gripper 161 can be transported to a free detection position 141B of the detection subunit 140B for detection, by linearly translating the movable vessel workstation 160. While moving the movable vessel workstation 160 between the dispensing position and a detection position 141B, the gripper can shake the vessel 10B for mixing the test liquid and the reagent of the second type contained therein. By parallel addition of an incubation reagent and a time-trigger reagent with the same pipetting head and by synergistic cooperation of the movable vessel workstation, the use of functional resources can be optimized and workflow efficiency can be increased with significant time savings, space savings and cost reduction. By holding the vessel 10B by the gripper 161 and pipetting a time-trigger reagent in the vessel 10B held by the gripper, the time between addition of the time-trigger reagent and start of detection can be minimized. By shaking the vessel 10B during transportation the time for mixing can also be minimized thus contributing to minimize the time between addition of the time-trigger reagent and start of the detection.

After parallel addition of the a reagent of the first type and a reagent of the second type into two vessels 10A, 10B at the first static vessel holder 140, the reagent pipette head 170' can move to the second static vessel holder 140' for dispensing the second reagent of the second type into a vessel 10 held by the vessel gripper 161' of the second static vessel holder 140'.

The vessel 10, 10A that has received a reagent of the first type can remain in incubation for one or more cycle times before receiving a reagent of the second type in a subsequent cycle time.

In one embodiment, the first static vessel holder 140 can be dedicated at least temporarily to a test type, e.g., to carry out APTT tests, whereas the second static vessel holder 140' can be dedicated to a different test type, e.g., to carry out PT tests. Thus in a cycle, parallel addition of an incubation reagent and a time-trigger reagent can take place at the first static vessel holder 140 into two respective vessels 10A, 10B in performance of two APPT tests at different stages respectively, followed by addition of a time-trigger reagent into a vessel 10 at the second static vessel holder 140', such as into a vessel held by the gripper 161' of the second movable vessel workstation 160', in performance of a PT test, the PT test requiring only a time-trigger reagent. The same procedure may be repeated in a subsequent cycle for different test liquids and vessels 10 respectively. The system 100' can be thus programmed to perform high-throughput analysis of two of the most frequently used tests in coagulation analysis.

With reference to the embodiment of FIGS. 1 and 5, the process can be similar, the difference being that there is one sample pipetting device 178 and two reagent pipetting device 175, 176 for a reagent of the first type and second type respectively on the same sample/reagent pipette head 170 and there is only one static vessel holder 140. The process of parallel addition and transportation of the vessel 10B held by the gripper 161 can otherwise be the same.

Obviously modifications and variations of the disclosed embodiments are possible in light of the above description. It is therefore to be understood, that within the scope of the appended claims, the present disclosure may be practiced otherwise than as specifically devised in the above examples.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A system for in-vitro diagnostic analysis, the system comprising:
    a vessel processing area comprising a first static vessel holder and a second static vessel holder and at least two movable vessel workstations, each movable vessel workstation comprising a vessel gripper;
    at least one sample pipette head comprising at least two sample pipetting devices, wherein the at least two pipetting devices each comprise at least one dispensing/aspiration nozzle to pipette test liquids;
    at least one reagent pipette head comprising at least three reagent pipetting devices, wherein the at least three pipetting devices each comprise at least one dispensing/aspiration nozzle to pipette reagents; and
    a controller programmed to control the at least two movable vessel workstation, the at least one sample pipette head, the at least two sample pipetting devices, the at least one reagent pipette head and the at least three reagent pipetting devices for executing a number of scheduled process operations, wherein the at least two movable vessel workstation, the at least one sample pipette head, and the at least one reagent pipette head are separate from each other.

2. The system for in-vitro diagnostic analysis according to claim 1, further comprises,
    a vessel input station configured to feed vessels to the first static vessel holder and the second static vessel holder.

3. The system for in-vitro diagnostic analysis according to claim 1, wherein the first static vessel holder and the second static vessel holder are dedicated to two different coagulation tests.

4. The system for in-vitro diagnostic analysis according to claim 3, wherein the two different coagulation tests are Prothrombin time (PT) test and the activated partial thromboplastin time (APTT) test.

5. The system for in-vitro diagnostic analysis according to claim 3, wherein the first static vessel holder is dedicated to the activated partial thromboplastin time (APTT) test.

6. The system for in-vitro diagnostic analysis according to claim 3, wherein the second static vessel holder is dedicated to the Prothrombin time (PT) test.

7. The system for in-vitro diagnostic analysis according to claim 1, wherein an incubation reagent and a time-trigger regent are added in parallel into two vessels at the first static vessel holder followed by addition of a time-trigger reagent into a vessel at the second static vessel holder.

8. The system for in-vitro diagnostic analysis according to claim 1, wherein the at least three reagent pipetting devices comprise one first reagent type pipetting device and two second reagent type pipetting devices.

9. The system for in-vitro diagnostic analysis according to claim 1, wherein the number of scheduled process operations comprises,
    the addition of a first reagent type to a first test liquid during a first cycle time,
    the addition of a second reagent type to the first test liquid during a second cycle time,
    the addition of the first reagent type to the first test liquid comprising parallel addition of a second reagent type to a second test liquid during the first cycle time, and
    the addition of the second reagent type to the first test liquid comprising parallel addition of the first reagent type to a third test liquid during the second cycle time, respectively.

10. A system for in-vitro diagnostic analysis, the system comprising:
    a vessel processing area comprising at least two static vessel holders and at least two movable vessel workstations, each movable vessel workstation comprising a vessel gripper;
    at least one sample pipette head comprising at least two sample pipetting devices, wherein the at least two pipetting devices each comprise at least one dispensing/aspiration nozzle to pipette test liquids;
    at least one reagent pipette head comprising at least three reagent pipetting devices, wherein the at least three pipetting devices each comprise at least one dispensing/aspiration nozzle to pipette reagents; and
    a controller programmed to control the at least two movable vessel workstation, the at least one sample pipette head, the at least two sample pipetting devices, the at least one reagent pipette head and the at least three reagent pipetting devices for executing a number of scheduled process operations comprising:
        the addition of a first reagent type to a first test liquid,
        the addition of a second reagent type to the first test liquid,
        the addition of the first reagent type to the first test liquid comprising parallel addition of a second reagent type to a second test liquid, and
        the addition of the second reagent type to the first test liquid comprising parallel addition of the first reagent type to a third test liquid, respectively.

11. The system for in-vitro diagnostic analysis according to claim 10, wherein the first reagent type is an incubation reagent and the second reagent type is a time-trigger reagent.

12. The system for in-vitro diagnostic analysis according to claim 10, wherein the first reagent type is for the determination of coagulation factors.

13. The system for in-vitro diagnostic analysis according to claim 10, wherein the first reagent type is for the determination of coagulation parameters.

14. The system for in-vitro diagnostic analysis according to claim 10, wherein the second reagent type is coagulation trigger reagent.

15. The system for in-vitro diagnostic analysis according to claim 10, wherein the second reagent type is a salt solution.

16. The system for in-vitro diagnostic analysis according to claim 15, wherein the salt solution is NaCl or CaCl2.

17. The system for in-vitro diagnostic analysis according to claim 10, further comprising,
   a reagent holding unit for holding reagents of the first reagent type and the second reagent type.

18. The system for in-vitro diagnostic analysis according to claim 17, wherein the at least three reagent pipetting devices aspire reagents from the reagent holding unit and dispense reagents into vessels in the vessel processing area.

19. The system for in-vitro diagnostic analysis according to claim 10, further comprising,
   a sample loading/unloading unit for loading/unloading sample tube racks comprising sample tubes.

20. The system for in-vitro diagnostic analysis according to claim 19, wherein the at least two sample pipetting devices aspire test liquids from sample liquids from the sample loading/unloading unit and dispense the test liquids into vessels in the vessel processing area.

* * * * *